United States Patent [19]

Brauker et al.

[11] Patent Number: 5,882,354
[45] Date of Patent: *Mar. 16, 1999

[54] CLOSE VASCULARIZATION IMPLANT MATERIAL

[75] Inventors: James H. Brauker, Harvard; Robert C. Johnson, Bartlett; Laura A. Martinson, Chicago; Ronald S. Hill, Grayslake, all of Ill.

[73] Assignee: Baxter International Inc., Deerfield, Ill.

[ * ] Notice: The term of this patent shall not extend beyond the expiration date of Pat. No. 5,782,912.

[21] Appl. No.: 480,198

[22] Filed: Jun. 7, 1995

Related U.S. Application Data

[62] Division of Ser. No. 210,068, Mar. 17, 1994, abandoned, which is a continuation of Ser. No. 933,871, Aug. 21, 1992, abandoned, which is a continuation of Ser. No. 735,401, Jul. 24, 1991, abandoned, which is a continuation-in-part of Ser. No. 606,791, Oct. 31, 1990, abandoned.

[51] Int. Cl.$^6$ .................................................. A61F 2/02
[52] U.S. Cl. ....................... 623/11; 623/1; 623/11; 623/66; 424/423; 424/425; 435/240.241; 435/284
[58] Field of Search ................... 424/422–425; 623/1–3, 10–12, 16, 18, 66; 435/284, 240.241

[56] References Cited

U.S. PATENT DOCUMENTS

| 3,967,618 | 7/1976 | Zaffaroni . |
|---|---|---|
| 3,993,072 | 11/1976 | Zaffaroni . |
| 4,011,861 | 3/1977 | Enger . |
| 4,229,838 | 10/1980 | Mano . |
| 4,266,999 | 5/1981 | Baier . |
| 4,298,002 | 11/1981 | Ronel et al. . |

(List continued on next page.)

FOREIGN PATENT DOCUMENTS

| 1196862 | 11/1985 | Canada . |
|---|---|---|
| 0 147 939 | 11/1983 | European Pat. Off. . |
| 0 127 989 | 12/1984 | European Pat. Off. . |
| 0 188 309 | 7/1986 | European Pat. Off. . |
| 0 216 149 | 8/1986 | European Pat. Off. . |

(List continued on next page.)

OTHER PUBLICATIONS

Bioengineering in Development of the Hybrid Artificial Pancreas; C.K. Colton et al., Transactions of the ASME, vol. 113, May 1991.

Texturing of Polmer Surfaces at the Cellular Level, J.A. Schmidt et at., Biomaterials, vol. 12, May, 1991.

Microtopography and Soft Tissue Response; C.E. Campbell et al., Journal of Investigative Surgery, vol. 2, pp. 51–74, 1991.

Macroporous Hydrogel Membranes for a Hybrid Artificial Pancreas. II. Biocompatibility; Klomp et al., Jrnl of Bomedical Mat. Res., vol. 17, 865–871 (1983).

Oxygen Tension Regulates the Expression of Angiogenesis Factor by Macrophages; Knighton et al., Science, 1981.

Macrophage–derived Growth Factors in Wound Healing: Regulation of Growth Factor Production by theOxygen Microenvironment; Knighton et al., Am. Rev. Respir. Dis. 1989; 140:1108–1111.

Activated Macrophages Induce Vascular Proliteration; Piverini et al., Nature, vol. 269, pp. 804–806, Oct. 27, 1977.

Japanes Abstract of 8078845 assigned to Fujisawa Pharm KK & Kyoto Ceramic KK.

(List continued on next page.)

*Primary Examiner*—John G. Weiss
*Assistant Examiner*—Francis K. Cuddihy
*Attorney, Agent, or Firm*—McDonnell Boehnen Hulbert & Berghoff

[57] ABSTRACT

A device for implantation in a host having a material at an interface between the host and the device, said material having a conformation which results in growth of vascular structures by the host close to the interface.

5 Claims, 7 Drawing Sheets

U.S. PATENT DOCUMENTS

| | | |
|---|---|---|
| 4,306,318 | 12/1981 | Mano et al. . |
| 4,309,776 | 1/1982 | Berguer . |
| 4,309,996 | 1/1982 | Theeuwes . |
| 4,321,711 | 3/1982 | Mano . |
| 4,352,883 | 10/1982 | Lim . |
| 4,353,888 | 10/1982 | Sefton . |
| 4,374,669 | 2/1983 | MacGregor . |
| 4,378,016 | 3/1983 | Loeb . |
| 4,391,909 | 7/1983 | Lim . |
| 4,475,916 | 10/1984 | Himmelstein . |
| 4,487,758 | 12/1984 | Goosen et al. . |
| 4,508,113 | 4/1985 | Malaney . |
| 4,542,539 | 9/1985 | Rowe et al. . |
| 4,553,272 | 11/1985 | Mears . |
| 4,576,608 | 3/1986 | Homsy . |
| 4,578,191 | 3/1986 | Jaffrin et al. . |
| 4,601,893 | 7/1986 | Cardinal . |
| 4,657,544 | 4/1987 | Pinchuk . |
| 4,664,669 | 5/1987 | Ohyabu et al. . |
| 4,670,286 | 6/1987 | Nyilas et al. . |
| 4,673,566 | 6/1987 | Goosen et al. . |
| 4,686,098 | 8/1987 | Kopchick et al. . |
| 4,689,293 | 8/1987 | Goosen et al. . |
| 4,712,553 | 12/1987 | MacGregor . |
| 4,743,252 | 5/1988 | Martin, Jr. et al. . |
| 4,795,459 | 1/1989 | Jauregui . |
| 4,798,585 | 1/1989 | Inoue et al. . |
| 4,803,168 | 2/1989 | Jarvis, Jr. . |
| 4,804,381 | 2/1989 | Turina et al. . |
| 4,806,355 | 2/1989 | Goosen et al. . |
| 4,816,339 | 3/1989 | Tu et al. . |
| 4,822,361 | 4/1989 | Okita et al. . |
| 4,871,366 | 10/1989 | Von Recum et al. . |
| 4,877,029 | 10/1989 | Valentini et al. . |
| 4,878,913 | 11/1989 | Aebischer et al. . |
| 4,892,538 | 1/1990 | Aebischer et al. . |
| 4,911,717 | 3/1990 | Gaskill, III . |
| 4,922,926 | 5/1990 | Hirschberg et al. . |
| 4,936,317 | 6/1990 | MacGregor . |
| 4,950,483 | 8/1990 | Ksander et al. . |
| 4,990,138 | 2/1991 | Bacich et al. . |
| 5,002,572 | 3/1991 | Picha . |
| 5,002,661 | 3/1991 | Chick et al. . |
| 5,024,670 | 6/1991 | Smith et al. . |
| 5,026,365 | 6/1991 | Rossini et al. . |
| 5,035,891 | 7/1991 | Runkel et al. . |
| 5,077,215 | 12/1991 | McSuslan et al. . |
| 5,104,403 | 4/1992 | Brotzu et al. ............ 623/1 |
| 5,182,111 | 1/1993 | Aebischer et al. . |
| 5,219,361 | 6/1993 | Von Recum . |

FOREIGN PATENT DOCUMENTS

| | | |
|---|---|---|
| 0 232 543 | 8/1987 | European Pat. Off. . |
| 02 59 536 | 3/1988 | European Pat. Off. . |
| 0 277 678 | 10/1988 | European Pat. Off. . |
| 02 13 908 | 3/1989 | European Pat. Off. . |
| 03 59 575 | 3/1990 | European Pat. Off. . |
| 0359575A | 3/1990 | European Pat. Off. ......... 623/11 |
| 03 70 292 | 5/1990 | European Pat. Off. . |
| 4006145 | 8/1990 | Germany . |
| 2 095 257 | 1/1981 | United Kingdom . |
| 2 185 408 | 7/1987 | United Kingdom . |
| WO 90/00888 | 7/1888 | WIPO . |
| WO 83/03536 | 10/1983 | WIPO . |
| WO 84/01287 | 4/1984 | WIPO . |
| WO 88/03785 | 6/1988 | WIPO . |
| WO 90/02580 | 9/1988 | WIPO . |
| PCT/US/89/ 00742 | 2/1989 | WIPO . |
| WO 89/03705 | 5/1989 | WIPO . |
| WO 91/00119 | 1/1991 | WIPO . |
| WO 91/19783 | 7/1991 | WIPO . |

OTHER PUBLICATIONS

Anderson J. "Inflammatory Responses to Implants," vol. XXXIV Trans. Am. Soc. Artif. Intern. Organs, 1988.

Christenson et al., "Tissue of Corticoid and Doxorubicin," J of Biomed Mat Res, 23, pp. 705–718 (1989).

Schrap, D. et al., "Islet Immuno–Isolation: The Use of Hybrid Artificial Organs to Prevent Islet Tissue Immuno–Isolation;" World J Surg 8 pp. 221–229 (1984).

Ratner, B., "New ideas in biomaterials science—a path to engineered biomaterials:" Journal of Biomedical Materials Research, vol. 27, pp. 837–850 (1993).

Weaver, J.M. et al., "The Growth of Cells in Diffusion Chambers. II. The Role of Cells in the Destruction of Homografts in Mice;" Journal of the National Cancer Institute, vol. 15 No. 6, pp. 1737–1764 (Jun. 1955).

Woodward et al., "The Tissue Response to Implants and its Evaluation by Light Microscopy;" CH 30, Handbook of Biomaterials Evaluation, Ed., pp. 364–378.

Miller et al., "Characterization of Biomedical Polymeradherent Macrophages: Interleukin 1 Generation and Scanning Electron Microscopy Studies", vol. 10, Apr. 1989 of Biomaterials, pp. 187–105.

Brauker, J. et al., Neovascularization at a Membrane–Tissue Interface is Dependent on Microarchitecture, New Ideas . . . : p. 846.

Freed, P.S., "Long–Term Percutaneous Access Device;" Trans AM Soc Artif Intern Organs, vol. XXXI, pp. 230–232 (1985).

Chehroudi, B. et al, "Effects of a grooved epoxy substratum on epithelial cell behavior in vitro and in vivo;" Journal of Biomedical Materials Research, vol. 22, pp. 459–473 (1988).

Eskin, S. G. et al., "Endothelial Cell Culture on Dacron Fabrics of Different Configurations;" Journal of Biomedical Materials Research, vol. 12, pp. 517–524 (1978).

Boyce, B., "Physical Characteristics of Expanded Polytetraflurorethylene Grafts; Biologic and Synthetic Vascular Prostheses," pp. 553–559 (1982).

Campebell, C. et al., "A Small Arterial Substitute: Expanded Microporous Polytetrafiroroethylene: Patency Versus Porosity;" Annals of Surgery, pp. 136–143 (1975).

Campbell, C.D., "Expanded microporous polytetrafluoroethylene as a vascular substitute: A two year follow–up;" Surgery 85, pp. 17701–17783 (1979).

Squier, C.A., "The relationship between soft tissue attachment, epithelial downgrowth and surface porosity;" Journal of Periodontal Research 16, pp. 434–440, 1981.

Wasfie, T. et al., "Inhibition of Epithelial Downgrowth on Percutaneous Access Devices inSwind: II;" Trans Am Soc Artif Intern Organs, vol. XXX, pp. 556–560, (1984).

Schruders, P. et al., "Normal wound healing compared to healing within proous Dacron Implants;" Journal of biomedical Materials Research, vol. 22, pp. 121–135 (1988).

Korsmeyer, R. et al., "Effect of the Morphology of Hydrophilic Polmeric Matrices on the Diffusionand Release of Water Soluble Drugs;" Journal ofMembrane Science, 9, pp. 211–227 (1981).

Reinhart, C. et al., "Solute diffusion in swollen membranes. Part II. Influence of crosslinking on diffusive properties;" Journal of Membrane Science, 18 pp. 227–239 (1984).

Iwata, H., "The use of photocrosslinkable polyvinyl alcohol in the immunoisolation of pancreatic Islets;" Transplantation Proceedings, vol. 22, No. 2 (Apr.), 1990 pp. 797–799.

Algire, G., "Diffusion–Chamber Techniques for studies of cellular immunity;" Annals New York Academy of Sciences, pp. 663–667.

Algire, G. et al., "Recent Developments in the Transparent–Chamber Technique as Adapted to the Mouse;" Journal of the National Cancer Institute, vol. 10 No. 2, pp. 225–253 (Oct. 1949).

Prehn, R.T. et al., "The Diffusion–Chamber Technique Applied to a Study of the Nature of Homograft Resistance;" Journal of the National Cancer Institute, vol. 15, No. 3, pp. 509–517 (Dec. 1954).

Algire, G. H. et al., "Growth of Cells in Vivo in Diffusion Chambers. I. Survival of Homografts in Immunized Mice;" Journal of the National Cancer Institute, vol. 15 No. 3, pp. 493–506 (Dec. 1954).

Merwin, R.M. et al., "Fate of Vascularized and Nonvascularized Subcutaneous Homografts in Mice;" Journal of the National Cancer Institute, vol. 14, No. 4, pp. 819–839 (Feb. 1954).

Islet Immuno–Isolation: The Use of Hybrid Artificial Organs to Prevent Islet Tissue Rejection, World J. Surg. 8, 221–229, 1984, D.W. Scharp et al.

CLOSE VASCULARIZATION IMPLANT MATERIAL

This is a divisional of application(s) Ser. No. 08/210,068 filed on Mar. 17, 1994, abandoned, which is a continuation of application Ser. No. 07/933,871 filed Aug. 21, 1992 (abandoned); which is a continuation of application Ser. No. 07/735,401 filed Jul. 24, 1991 (abandoned); which is a continuation-in-part of application Ser. No. 07/606,791 filed Oct. 31, 1990 (abandoned).

BACKGROUND OF THE INVENTION

The present invention relates to material implanted in a host. More particularly, the present invention relates to material that promotes the formation of vascular structures at the interface between at least a portion of the implanted material and the host.

For a variety of applications, ranging from research to therapeutic, it may be desirable to implant an article or device within soft tissue. Such implants can include indwelling catheters, indwelling sensors, and devices for holding tissue that are implanted in vivo.

If the implanted device is utilized to hold tissue, in a variety of such applications it is necessary to isolate the implanted tissue from the immune response of the host (immunoisolation). For example, this is critical when the implanted tissues are xenografts, i.e., graft cells from donors of another species, or allografts, i.e., cells from the same species but having a different genetic make-up. A failure to properly isolate such tissue will result in an invasion from host cells or host immunogenic factors rejecting the implant cells. In certain other applications, such as autografts, i.e., cells previously isolated from the tissue of the patient to be implanted, it is necessary to isolate the implanted tissues from the host, not because the cells would be rejected, but because the cells may contain retroviral vectors which otherwise might present a risk to the patient. Accordingly, it may be necessary for such cells to be enclosed within a structure that prevents the passage of cells therethrough.

In certain other implant applications it may be desirable to provide a zone or structure that is selectively impermeable for molecular diffusion as in certain forms of cellular implants that could be rejected by humoral factors, or non-permeable for non-transport functions, such as providing a surface for transcutaneous catheters.

When biomaterials are implanted, the host inflammatory cells (macrophages, giant cells, and fibroblasts) produce an inflammatory response called a foreign body response. This response invariably results in a zone of nonvascular tissue that surrounds the implanted material. The foreign body response is the body's attempt to remove or isolate the foreign entity (Anderson, J. M., "Inflammatory Response to Impants", Trans. Am. Soc. Artif. Interm. Ograns, Vol. XXXIV:101–107 (1988)).

During the foreign body response, macrophages from the host attempt to ingest the foreign body. In some cases, the macrophages coalesce to form multinuecleated giant cells. The implant may lead to the formation of fibroblast layers of increased thickness and density as the host attempts to isolate the foreign body. This creates a fibrous capsule of cells and collagen.

Referring to FIG. 1, a micrograph (1(*a*)) and a drawing (1(*b*)) are provided to illustrate a classical tissue response to an implanted foreign body. FIG. 1 represents a typical histological section taken through a tissue block removed after approximately three weeks from a dorsal subcutaneous implant in a Sprague-Dawley rat. As illustrated, the implant 10 is surrounded by a foreign body capsule 12 that forms adjacent to the implant. The foreign body capsule 12 typically consists of three-layers.

As illustrated, the first layer 13 of the foreign body capsule 12 includes macrophages 14 and foreign body giant cells 16 at an interface 18 between the implant 10 and the tissue. This first layer 13, consisting of the macrophages 14, is generally approximately 5 to about 15 microns thick.

The next, or second layer 15, of the foreign body capsule 12 includes fibroblasts 20. The fibroblasts 20 are oriented parallel to the surface of the implant 10 and embedded in a collagenous matrix including collagen fibers that are also oriented parallel with the surface of the implant. The second layer 15 consisting of the fibroblasts 20 and collagen fibers is generally approximately 30 to about 200 microns thick. The first and second layers 13 and 15 of the foreign body capsule 12 are usually completely avascular throughout.

At the outlying areas of the foreign body capsule 12, a few vascular structures 24 begin to appear in the outer regions of the fibroblast second zone 15. At a third layer 17, lying approximately 30 to about 200 microns away from the surface of the implant 10 is loose connective tissue that is highly vascular. This layer 17 is amorphous and widely varies in thickness depending on the tissue location and time after the implant.

As illustrated in FIG. 1, the classical foreign body response results in the implant 10 being surrounded by a foreign body capsule 12 that does not include vascular structures near the surface of the implant.

Although the foreign body capsule generated from the foreign body response is desirable, or at least not detrimental, for certain types of implants, such as, for example, silicon breast implants and collagen implants, the foreign body capsule prevents certain applications and treatments utilizing such implants. For example, indwelling sensors for applications such as glucose analysis in diabetics, become occluded after only a few days due to the foreign body capsule. Indeed, the foreign body capsule becomes so thick that it inhibits the diffusion of glucose to the membrane surface preventing the sensor from functioning.

Likewise, when pancreatic islets are implanted within a semipermeable membrane for treatment of diabetes, they usually die within a few days or weeks. The loss of function of the pancreatic islets is attributed to the poor diffusion of nutrients to the islets due to the thickness of the foreign body capsule. Likewise, other tissues that are implanted within the host do not remain viable due to the foreign body capsule that effectively prevents the transport of nutrients from the capillaries to cells enclosed within the implanted membrane.

Scharp, in a comprehensive review of the literature about immunoisolation ("Isolation and Transplantation of Islet Tissue" (1984) World J. Surgery 8:143–151) cited 18 papers on islet immunoisolation. In every case, the islets failed to function for more than a few weeks, or in 4 studies, several months. In every case but one, the failure was attributed to fibroblastic overgrowth of the membrane and chamber. The authors state that, "If . . . a [membrane] can be constructed to resist host fibrotic response, then the extravascular diffusion chamber approach may be useful clinically." They further state that the "primary disadvantages [of diffusion chambers] relate to the host fibroblastic response to the device." This belief is echoed in U.S. Pat. No. 4,298,002 which states, "the device . . . remains effective for limited periods of time because the body encapsulates the device with fibrous material blocking the passage of insulin, nutrients, and/or waste products."

More recent papers continue to state that device failure is caused by the foreign body capsule diminution of diffusion. For example, Christenson, Abeischer, McMillan, and Galletti, in "Tissue Reaction to Intraperitoneal Polymer Implants: Species difference and effects of corticoid and doxorubicin" ((1989) J. of Biomed. Mat. Res. 23:705–718) stated, "reduction of the tissue reaction around an implant is important in improving the long-term viability of the encapsulated endocrine tissue and is imperative for any clinical application of this technique for implanting endocrine tissue."

Poor viability of tissues has prompted the design of modalities for periodic replacement of implanted islets through percutaneous catheters (e.g. U.S. Pat. No. 4,378, 016) to solve the shortcoming of previous designs, i.e., the deterioration of implanted tissues because of overgrowth by a fibrous capsule.

Additionally, indwelling catheters that have a variety of applications, typically have a high drop-out rate because the site of the catheter entry becomes infected. It is generally believed that this infection is caused by poor adhesion of the tissues to the catheter surface and poor vascularization of the region around the catheter because of the thick foreign body capsule that forms. Implants have been proposed having surfaces designed to increase the adhesion or anchorage of the implant in the host tissue (e.g. European Patent Application No. 0359575 of Von Recum and Campbell). This patent application describes materials with surface topography designed to provide "improved soft tissue implant having a surface texture that optimizes anchorage of the implant to the tissue without causing inflammatory tissue at the implantation site."

In attempting to provide needed nutrients to cells and tissues located within implanted devices and/or allowing agents generated by the tissues to enter the host, an almost contradictory concern must be dealt with. For devices that include xenografts or allografts, these tissues must be isolated from the immune system of the host. Therefore, although it may be desirable to somehow connect the vascular system of the host to these tissues to provide nutrients and allow a transfer of biological agents to the host, a contrary concern is to prevent an immune response from the host to the tissues. Likewise, with respect to sensors and catheters, although it may be desirable to create vascularization with respect to these devices, vascularization into an interior of such devices will prevent the devices from functioning satisfactorily.

SUMMARY OF THE INVENTION

This present invention provides an implant material that results in close vascularization by the host at the interface between the material and the host into which the material is implanted.

The uses of the material of the present invention include: as a coating for indwelling catheters; means for transport of physiological factors to indwelling sensors; means for transport of drugs from a chamber or catheter to the tissues of the host; and means for encapsulation of grafted cells for treatment of cell and molecular deficiency diseases (immunoisolation).

In an embodiment, the present invention provides an asymmetric material having a first zone that induces close vascularization at the material host interface and a second adjacent zone that prevents passage of cells through the zone. The vascularizing zone allows the material to be vascularized while the second zone maintains immunoisolation of the interior of an implanted device incorporating the invention on its exterior. The material may consist of a bilayer of zones as described or it may be a gradient of zones. The gradient consists of an outer zone with a conformation that results in close vascularization. The structure of the material becomes gradually tighter until the material is impermeable to cells.

In another embodiment, the second adjacent zone is molecular permeable for selective diffusion. In yet another embodiment the second zone is non-permeable for use in non-transport functions in devices such as indwelling catheters.

To these ends, the present invention provides an implant having a three dimensional conformation or architectural structure at the host interface which allows invasion of the material by mononuclear cells, but prevents the invasion by connective tissue which leads to foreign body capsule formation within the structure.

Applicants do not fully understand how the close vascularization of the present invention occurs. The data presented in the tables and figures which follow are consistant with the theory that close vascularization occurs if the three dimensional conformation of material interfacing the host is such that it elicits certain host inflammatory cell behavior. Applicants have observed by light and electron microscopy that close vascularization occurs if in the initial period of implantation, at least some macrophages entering the material are not activated. Activated macrophage are characterized by cell flattening. Applicants observe close vascularization in regions of an implant where the macrophgages that have entered the cavities of the material retain a rounded appearance when viewed through light microscopy (~400×). See FIG. 2a. At 3000× (TEM) the rounded macrophage is observed to have substantially conformed to the contours of the material. Although there is a correlation with macrophage shape, it is not clear that macrophages control the observed response. However, it is clear that invasion of the structure by host cells is required. Although the bulk of the cells appear to be macrophages, it is possible that other inflammatory cells control the response, therefore we will refer to the invading cells as "inflammatory cells," which include but are not limited to macrophages.

On the other hand foreign body capsule formation occurs when, in the initial period of implantation, inflammatory cells in contact with the implant material flatten against those portions of the material which present an area amenable to such flattening behavior by an inflammatory cell (FIG. 6).

In an embodiment, the material that results in formation of close vascular structures is a polymer membrane having an average nominal pore size of approximately 0.6 to about 20 $\mu$m, using conventional methods for determination of pore size in the trade. Preferably, at least approximately 50% of the pores of the membrane have an average size of approximately 0.6 to about 20 $\mu$m.

The structural elements which provide the three dimensional conformation may include fibers, strands, globules, cones or rods of amorphous or uniform geometry which are smooth or rough. These elements, hereafter referred to as "strands," have in general one dimension larger than the other two and the smaller dimensions do not exceed five microns.

In an embodiment, the material consists of strands that define "apertures" formed by a frame of the interconnected strands. The apertures have an average size of no more than about 20 μm in any but the longest dimension. The apertures of the material form a framework of interconnected apertures, defining "cavities" that are no greater than an average of about 20 μm in any but the longest dimension. In an embodiment the material has at least some apertures having a sufficient size to allow at least some vascular structures to be created within the cavities. At least some of these apertures, while allowing vascular structures to form within the cavities, prevent connective tissue from forming therein because of size restrictions.

In an embodiment, an asymmetric material is provided having a gradient or layer of varying porosity. At least some of the apertures at the surface of the material that contacts the host tissue, allow inflammatory cells to enter the cavities. But, due to size restrictions, the apertures do not allow the inflammatory cells to transverse the material to the interior of the implant.

In an embodiment of the present invention, an immunoisolation container is provided that includes a first membrane having cavities and situated proximal to the host tissue. At least some of the apertures of the first membrane have a sufficient size to allow inflammatory cells to enter the cavities and cause at least some vascular structures to contact the membrane. The container includes a second porous membrane, the apertures of the second membrane being sufficiently small to prevent immune cells and/or immunogenic factors from entering an interior of the container. The second membrane is situated proximal to graft tissues.

In an embodiment, an indwelling catheter is provided by the present invention including a porous membrane and a catheter body, the porous membrane surrounding at least a portion of the catheter body. At least some apertures of the porous membrane have a sufficient size to allow inflammatory cells to enter the cavities and cause at least some vascular structures to form that contact the porous membrane.

In an embodiment, the present invention provides an indwelling sensor. The indwelling sensor comprising a sensor for monitoring a condition or agent in the body and a porous membrane that surrounds at least a portion of the sensor body. At least some of the apertures of the membrane have a sufficient size to allow inflammatory cells to enter the cavities and cause at least some vascular structures to form that contact the porous membrane.

The present invention also provides a method for the vascularization of a surface of an implanted device. The method comprises the steps of allowing inflammatory cells to enter a first layer of a membrane structure and cause vascular structures to form that contact a surface of the first layer of the membrane and preventing the inflammatory cells from entering a second layer of the membrane structure. This embodiment would be applicable in, for example, a breast prothesis.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention provides a material for inducing close vascularization at the interface between the material and host into which the material is implanted such that a standard foreign body capsule consisting of flattened macrophages, foreign body giant cells, and fibroblasts does not intervene between the vascular structures and the material. The material can be utilized for various applications including the creation of a container for implanting tissues to be isolated from the immune system of a host, for surrounding a portion of a catheter, or surrounding a portion of an indwelling sensor device.

Pursuant to the present invention, the material utilized results in the growth of vascular structures close to or immediately adjacent to the material. As used herein, close vascular structures or vascular structures that contact, are those capillaries whose surface lies within about one cell layer of the surface of the material. When implants including the materials of the present invention are implanted within a host a foreign body-like capsule still forms in response to the implantation. However, its structure is greatly altered due to the host response to the material. In contrast to a standard foreign body response, a vascular bed forms at the host-material interface.

Figure 2A:
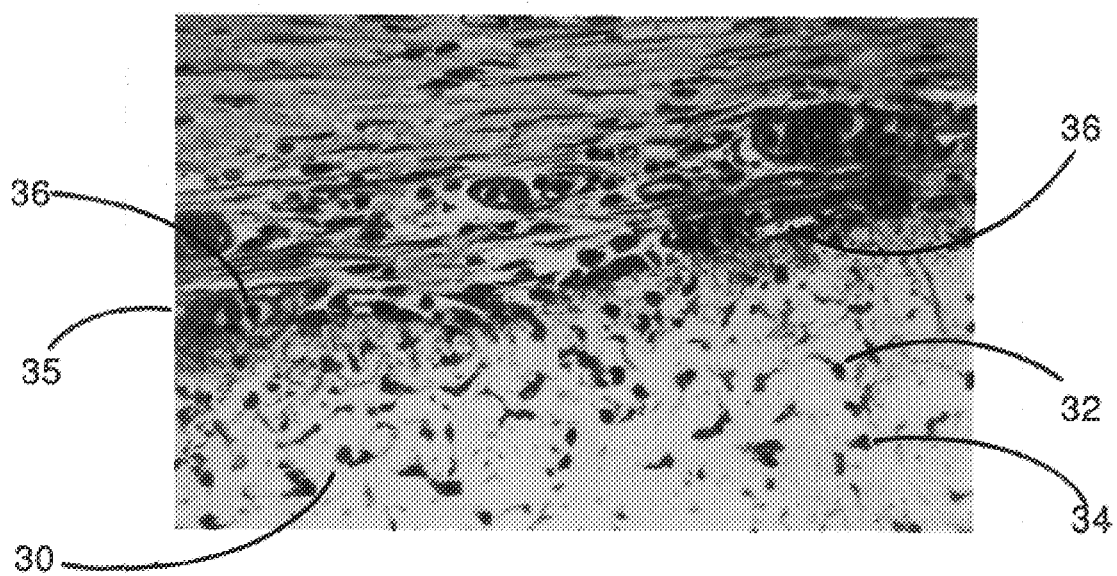
FIG. 2(a) is a micrograph of an embodiment of the present invention.
Figure 2B:
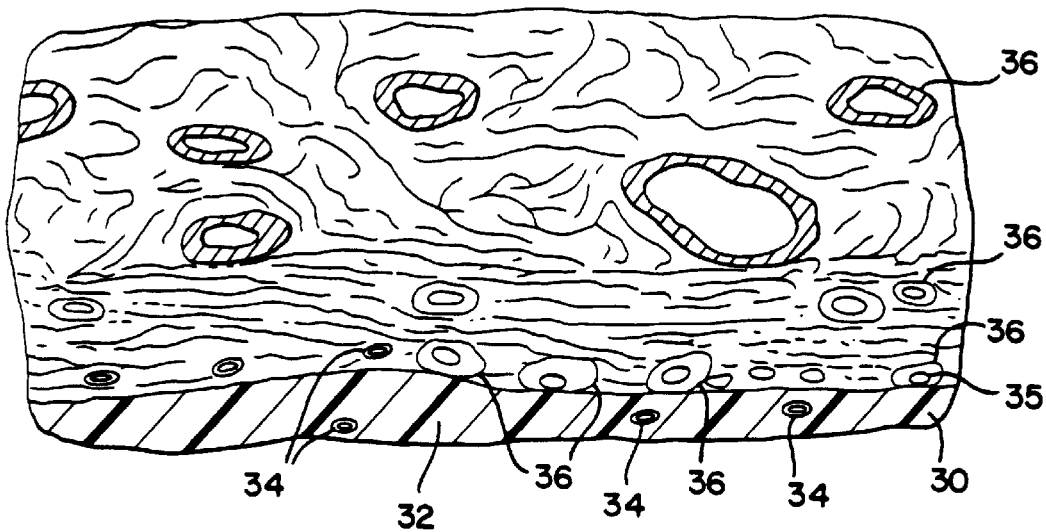
FIG. 2(b) is a cross-sectional view of an embodiment of the present invention with vascular structures growing at the host-material interface.

Referring now to FIG. 2, an embodiment of the present invention is illustrated. In this embodiment, a polymer membrane 30 at least partially surrounds an implant and includes three dimensional cavities 32. At least some of the cavities 32 of the membrane 30 have a sufficient size and structure to allow inflammatory cells 34 to completely enter therein through the apertures that define the cavities, and are defined by frames composed of strands that are less than five microns in all but the longest dimension. When the inflammatory cells 34 enter the cavities 32, growth of vascular structures 36 occurs within about one cell layer from the interface 35 of the membrane 30 and host. Although not required, vascular structures may be formed within the irregularities 32 of the membrane. Accordingly, although a foreign body-like capsule of fibroblasts still forms that surrounds the membrane 30, the entire foreign body-like capsule, including fibroblast layers, is well vascularized. The formation of close vascular structures is dependent on entry of the inflammatory cells into the cavities of the membrane so that the cells are surrounded by the strands that define the apertures and cavities. The topographic features at the implant surface do not effect the morphology of the inflammatory cells. Indeed, inflammatory cells at the implant surface often maintain a flat morphology.

In selecting the size and shape of the strands and cavities 32 for the material 30 of the present invention, it must first be appreciated that not all of the cavities must have a sufficient size to allow inflammatory cells 34 to enter therein. What is required is that a sufficient number of cavities 32 have a size that allows a sufficient number of inflammatory cells 34 to enter therein. Nor is it necessary that all of the strands be less than five microns in all but the longest dimension. Some strands may be longer, as long as a sufficient number of the strands are within the prescribed size limits. The presence of a sufficient number of strands and cavities of the prescribed size creates a sufficient number of vascular structures at the host-material interface. These vascular structures will provide sufficient nutrients to an immunoisolated container and/or allow components and agents produced by cells within the interior of the chamber to enter the host.

Figure 3:
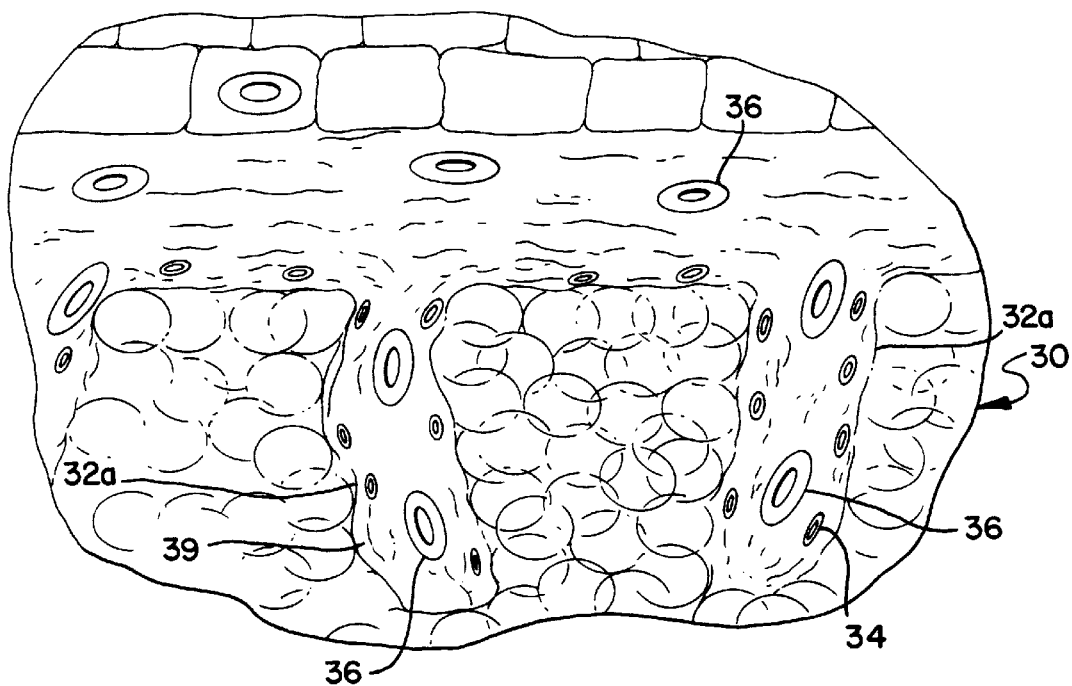
FIG. 3 illustrates a cross-sectional view of a foreign body capsule in a pore of a membrane.

Although at least some of the cavities 32 must have a sufficient size and shape to allow inflammatory cells 34 to enter therein, it is also important that extensive ingrowth of vascular and connective tissues within the cavities 32 does not occur. As illustrated in FIG. 3, in the case where the apertures and cavities are too large, an extensive growth of vascular tissue 36 and connective tissue 39 occurs within a large cavity 32a; this causes the vascular tissue to be isolated within the large cavity. The isolation of the vascular tissue 36 within the large cavity 32a by fibroblasts and connective tissues 39 is similar to the standard foreign body response previously discussed. By selecting cavities 32 of appropriate size, one can prevent the formation of fibroblasts and connective tissue 39 therein.

It has been found that a porous polymer membrane having an average nominal pore size of approximately 0.6 to about 20 microns and average strand sizes of less than about five microns in all but the longest dimension, functions satisfactorily in creating a vascular bed at the tissue-membrane interface. It should be noted, that the term "nominal pore size" is derived from methods of analysis common to the membrane trade, such as the ability of the membrane to filter particles of a particular size, or the resistance of the membrane to the flow of fluids. Because of the amorphous, random and irregular nature of most of these commercially available membranes, the "pore" size designation does not actually indicate the size or shape of the apertures and cavities, which in reality have a high degree of variability. The cavities are not really "pores" in that they typically are not uniform regular holes or channels through the material. Instead, these commercial membranes can be composed of, for example, extruded filaments which act as sieves as shown, for example, in FIG. 4b. Accordingly, as used herein the term "pore size" is a manufacturer's convention used to identify a particular membrane of a particular commercial source which has a certain bubble point. As used herein, the term "pore" does not describe the size of the cavities of the material used in the instant invention. The bubble point measurement is described in Pharmaceutical Technology May 1983 pp. 36 to 42.

As previously noted, it is not critical that all of the apertures 32 (FIG. 2) of the material 30 allow inflammatory cells 34 to penetrate the material or, conversely prevent connective tissues from forming within the cavities. What is required is that a sufficient number of the cavities 32 have a size that allows inflammatory cells 34 to enter therein and yet prevent connective tissue from forming therein. In the materials tested by Applicants the desired result is obtained where the strands that define the apertures of the cavities have a size of less than about five microns in all but the longest dimension. It has been determined that a commercially available membrane having at least approximately 50% of its cavities with an average nominal size of approximately 0.6 to about 20 microns and strands having an average size of less than about five microns in all but the longest dimension will function satisfactorily in creating vascular structures close to the membrane.

By way of example, and not limitation, the following experiments were performed on commercially available membranes to determine which membranes result in the close vascularization of the present invention.

Numerous commercially available membranes with varying nominal pore sizes were implanted in subcutaneous pockets on the backs of adult male Sprague Dawley rats for three weeks, and examined histologically. The results, shown in Tables 1–3, were that all membranes with apertures too small or having strands too closely associated to allow penetration of macrophages (Table 1) had standard foreign body capsules (i.e., similar to that illustrated in FIG. 1), whereas many membranes with apertures large enough to allow macrophages to penetrate (Table 2) had close vascular structures (i.e., similar to that illustrated in FIG. 2).

TABLE I

MEMBRANES THAT ARE NOT INVADED BT CELLS AND DO NOT HAVE CLOSE VASCULAR STRUCTURES

| Company | Membrane | Nominal Pore Size |
| --- | --- | --- |
| Millipore | Mixed Esters Cellulose | 0.1 |
| Millipore | Mixed Esters Cellulose | 0.22 |
| Millipore | Mixed Esters Cellulose | 0.45 |
| Celenase | polypropylene | 0.05 |
| Celenase | polypropylene | 0.075 |
| Gore | PTFE/Polyester | 0.02 |
| Gore | PTFE/Polyester | 0.2 |
| Akzo | polypropylene | 0.01–0.29 |
| Akzo | polypropylene | 0.02–0.58 |
| Akzo | polypropylene | 0.1 |
| Akzo | polypropylene | 0.08 |
| Akzo | polypropylene | 0.6 |
| Supor | polysulfone | 0.1 |
| Amicon | YC, YM, PM, XM | 10–300 kD |
| Omega | polyethersulfone | 100–30okD |
| Millipore | Durapore ® | 0.22 |
| Millipore | Immobilon-n ® | 0.22 |
| Gelman | Versapore ® | 0.22 |
| Gelman | Supor ® | 0.22 |
| Gelman | Supor ® | 0.8 |
| Gelman | Polysulfone HT-200 | 0.22 |
| Gelman | Polysulfone HT-200 | 0.6 |
| Gelman | Polyester | 0.22 |
| Gelman | Polysulfone/polyester | 0.8 |
| Sartorius | Cellulose Acetate | 0.22 |
| Sartorius | Cellulose Acetate | 0.22 |
| Sartorius | Cellulose Acetate | 0.45 |
| Sartorius | Cellulose Acetate | 0.65 |
| Sartorius | Cellulose Nitrate | 0.22 |
| Sartorius | Reinforced Cell. Acet. | 0.22 |
| Nucleopore | Polyester | 0.8 |
| Pall | Uncharged Nylon | 0.22 |
| AMF Cumo | Charged Nylon | 0.22 |
| Micron Separation Inc. | Nylon 66 | 0.22 |

TABLE I-continued

MEMBRANES THAT ARE NOT INVADED BT CELLS AND
DO NOT HAVE CLOSE VASCULAR STRUCTURES

| Company | Membrane | Nominal Pore Size |
|---|---|---|
| Micro Filtration Sys. | Cellulose Acetate | 0.22 |
| Micro Filtration Sys. | Cellulose Acetate | 0.22 |
| Akzo | Polypropylene-HF | 0.2–0.8 |

TABLE 2

MEMBRANES THAT ARE INVADED BY CELLS
AND HAVE CLOSE VASCULAR STRUCTURES

| Company | Membrane | Nominal Pore Size |
|---|---|---|
| Millipore | Mixed Esters Cellulose | 1.2 |
| Millipore | Mixed Esters Cellulose | 8.0 |
| Sartorius | Cellulose Acetate | 0.8 |
| Sartorius | Cellulose Acetate | 1.2 |
| Sartorius | Cellulose Acetate | 3.0 |
| Sartorius | Cellulose Acetate | 5.0 |
| Sartorius | Cellulose Acetate | 8.0 |
| Gore | PTFE/Polyester | 1.0 |
| Gore | PTFE/Polypropylene | 3.0 |
| Gore | PTFE/Polyester | 3.0 |
| Gelman | Versapore ® | 0.8 |
| Gelman | Versapore ® | 1.2 |
| Gelman | Versapore ® | 3.0 |
| Gelman | Versapore ® | 5.0 |

TABLE 3

MEMBRANES THAT ARE INVADED BY CELLS
BUT DO NOT HAVE CLOSE VASCULAR STRUCTURES

| Company | Membrane | Nominal Pore Size |
|---|---|---|
| Tetco | Polyester | 3 |
| Tetco | Polyester | 5 |
| Tetco | Polyester | 8 |
| Tetco | Nylon | 10 |
| Tetco | Nylon | 10 |
| Tetco | Nylon | 10 |
| Millipore | PTFE | 5 |
| Millipore | PTFE | 10 |
| Nucleopore | Polycarbonate | 1 |
| Nucleopore | Polycarbonate | 3 |
| Nucleopore | Polycarbonate | 8 |
| Nucleopore | Polycarbonate | 12 |

For example, membranes created from mixed esters of cellulose and having nominal pore sizes of 0.1, 0.22, and 0.45 microns did not induce close vascular structures when subcutaneously implanted into rats. However, mixed esters of cellulose membranes with nominal pore sizes of 1.2 and 8 microns did induce close vascular structures. Similarly, cellulose acetate membranes having a nominal pore size of 0.2, 0.45, and 0.65 microns and teflon membranes having a nominal pore size of 0.02 and 0.2 microns did not induce close vascular structures. But, cellulose acetate membranes having a nominal pore size of 0.8, 1.2, 3, 5, and 8 microns, and teflon membranes having a nominal pore size of 1.0 and 3.0 microns did induce close vascular structures.

In membranes wherein close vascular structures were seen, the membrane was penetrated by inflammatory cells from the host. It is believed that the formation of close vascular structures is related to cellular invasion. However, numerous membranes that did allow penetration of inflammatory cells did not have close vascular structures (Table 3), indicating that invasion by inflammatory cells was perhaps related, but, not necessarily sufficient for the production of close vascular structures.

Figure 4A:
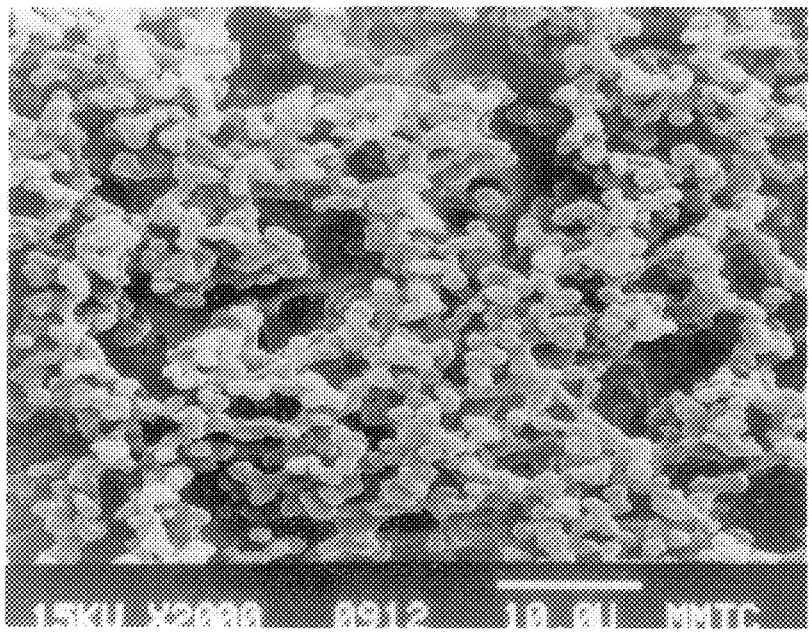
FIGS. 4(a) and (b) are scanning electron micrographs of, respectively, a mixed ester of cellulose membrane with a 5 μm pore size and a teflon membrane with 3 μm pore size.
Figure 4B:
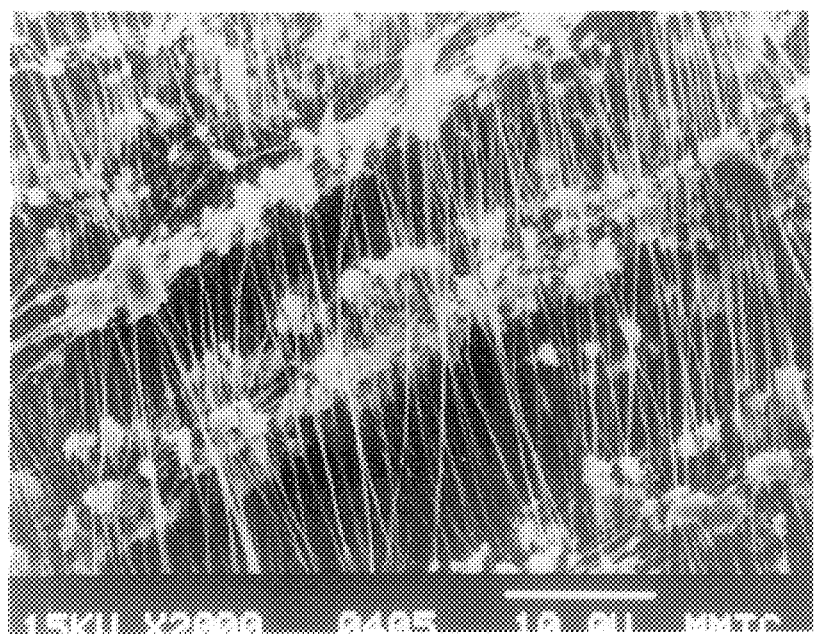

Scanning Electron Microscope (SEM) analysis of the membranes revealed three dimensional structural or architectural properties that distinguish membranes that do have close vascular structures (positive response) from those that do not (negative response). Membranes with a positive response had high porosities and were composed of strands (fibers, filaments, microglobules, cone-like or rod-like structures with a small diameter (<5 microns)). For example, Millipore brand mixed esters of cellulose membranes with nominal pore size of 5 μm are composed of irregular, amorphous globular structures and strands with diameters from about 1 to 3 μm, and irregular cavities from 0.5 to 5 microns in diameter, and having a percent porosity of 75% (FIG. 4a). Gore® teflon membranes with a nominal pore size of 3 μm are composed of strands with diameters of less than about 1 micron that interconnect with teflon clusters less than about 3 microns in diameter (FIG. 4b). The cavities are very elongated being generally about 1 to 2 microns wide by 10 to 15 μm long. After implantation, both of these membranes were invaded by inflammatory cells which had a round morphology under the light microscope (see invading cells in FIG. 2), and both consistently had close vascular structures.

Figure 5A:
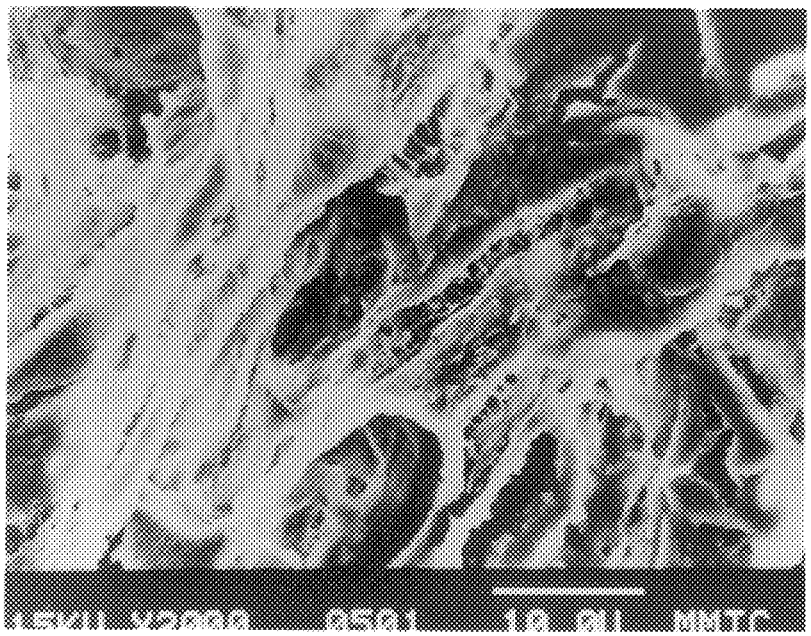
FIGS. 5(a) and (b) are scanning electron micrographs of, respectively, a teflon membrane with a 5 μm pore size and a polycarbonate with 12 μm pore size.
Figure 5B:
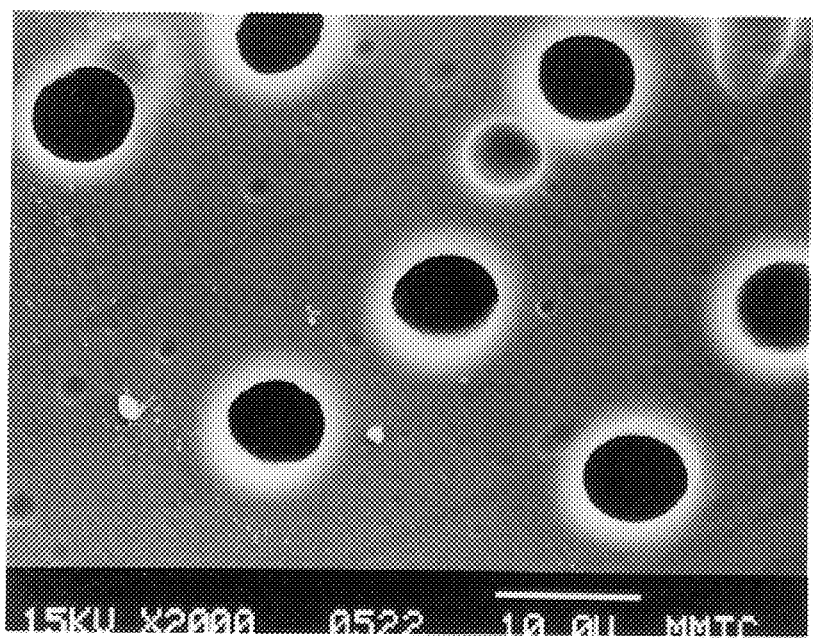

In contrast, membranes with a negative response had apertures and cavities defined by strands with a relatively high surface area, large enough for inflammatory cells to use as a substrate to flatten against. For example, Millipore brand teflon membranes with a nominal pore size of 5 microns (FIG. 5a) are composed of globular or plate-like structures about 5 to 10 microns in diameter, and have irregular amorphous cavities about 5 to 10 microns in diameter. Nuclepore brand membranes with a nominal pore size of 12 microns (FIG. 5b), have uniform circular holes that are 9 microns in diameter that are scattered within a membrane sheet, with from 5 to 25 microns between the edges of the holes. After implantation, both of these membranes were invaded by cells but the cells maintained a flattened morphology (see invading cells in FIG. 6).

Thus, the three dimensional conformation or architecture of the structures that delimit the cavities and irregularities have a strong influence on the biological response.

Applicants have further determined that materials with a positive response had structural features that caused penetrating cells to assume a round morphology. Whereas materials with a negative response had structural features that caused penetrating cells to assume a relatively flattened morphology.

Figure 6:
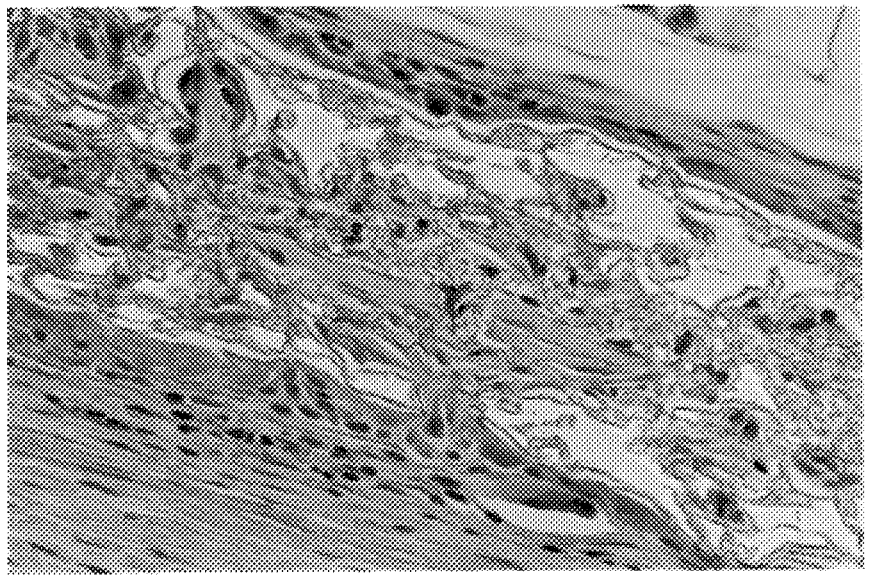
FIG. 6 illustrates a light micrograph showing the teflon membrane of FIG. 5(a) implanted for 3 weeks in a subcutaneous dorsal pocket in a rat.

Membranes with a negative response have a standard foreign body capsule after implantation, and were invaded by inflammatory cells that assumed an elongated, highly flattened morphology (FIG. 6). FIG. 6 is a light micrograph illustrating a teflon membrane (the same membrane illustrated in FIG. 5a) implanted for 3 weeks in a subcutaneous dorsal pocket in a rat. Note the extensive cytoplasm of the cells invading the polytetrafluoroethylene ("PTFE") membrane shown in FIG. 6. The cells appear to have flattened against the plate-like PTFE structure and have the appearance of cells of a standard foreign body response (FIG. 1) in contrast to the rounded cells invading the membrane in FIG. 2.

This is consistent with the observation of rounded mononuclear cells invading an implant during the early, acute phase of a foreign body response, followed by flattened cells on the surface of implants in the later, chronic standard foreign body response to implants with a smooth surface (e.g., FIG. 1). The flattening of the macrophages and foreign body giant cells against the surface walls off the implant, is followed by a quiescent, chronic response characterized by a lack of new invading mononuclear cells and a lack of new vascular growth in the periphery of the foreign body. Macrophages and foreign body giant cells from the initial host reaction to the implant remain, but are generally flattened against the foreign material. This is a long-term response that results in a permanent walling off of implants that are non-digestible by the macrophage. The maintenance of a long-term foreign body response is characterized by inflammatory cells which spread upon and cover the foreign material. Applicants have discovered that this response appears to require a surface-like area capable of acting as a substrate for flattening and spreading of the cells.

When the implanted material has an architecture of strands that have a diameter (<5 μm) too small or configuration too irregular to allow a surface for flattening of cells, as do the membranes that give a positive vascular response (FIG. 2 and Table 2), the efforts of the inflammatory cells to cover and wall off the material are thwarted, and the cells do not obtain a flattened morphology. Instead, they remain rounded and Applicants hypothesize that the inflammatory cells induce the formation of close vascular structures at the material-host interface. The implanted material is never completely walled off, and therefore a chronic response is never obtained.

Flattening and activation of inflammatory cells (which leads to foreign body capsule formation) is observed where the implant material provides a structure onto which the inflammatory cells can flatten and spread. An inflammatory cell does not require a smooth area for flattening. For example, an area composed of closely adjacent pillars of equal height and diameter might be recognized by the inflammatory cell as essentially "smooth" and the cells would then spread on the surface.

Applicants further hypothesize that if the inflammatory cell nucleus cannot enter a cavity or irregularity then the cell will "see" the material as flat and will flatten onto the material at that location. Conversely, cells in contact with a cavity or irregularity from more than one direction or plane will not "see" a flat area and will retain a rounded conformation or even conform to the shape of the cavity or irregularity. Accordingly, material having a surface-like area greater than about 5 microns would not be likely to result in close vascularization. For example, the material shown in FIG. 5a which gave a negative response has many cavities and irregularities which are smaller than about 6 um, but it also has leafy-appearing somewhat flat structures onto which macrophage may flatten. Accordingly, in the present invention material must be selected so that it has sufficient irregularities and cavities to prevent substantial numbers of inflammatory cells from flattening. The rounded cell may conform to the cavities and irregularities but will not flatten. Formation of some flattened cells, especially at the "surface" of the implant is often seen and is within the scope of the invention provided that there are not so many flattened cells that the material is walled off by nonvascularized fibroblasts.

Macrophage behavior is not yet fully understood. It is believed that macrophages are activated when they become flat. Upon activation they are believed to secret factors which signal fibroblasts to form and proliferate. Accordingly, Applicants hypothesize that by utilizing a material whose three dimensional cavities and irregularities prevent the macrophage from flattening, this invention will avoid macrophage activation and consequent formation of the typical foreign body capsule. On the other hand, it may be that rounded macrophages are secreting factors that either stimulate neovascularization directly or interrupt an existing suppression of new vascularization.

The host inflammatory cell response described above for the various materials is generally observed for up to about 12 weeks following implantation. Thereafter, in both the standard foreign body capsule response and in the use of the instant invention, the inflammatory cells gradually diminish leaving either a stable foreign body capsule or, in the instant invention, a stable vascularized bed. The Applicants have observed a stable vascular bed for 1.5 years in subcutaneous implants of 3 μm Gore® teflon in rats.

When the material utilized has the three dimensional architecture set forth above, a vascularized membrane is achieved. To this end, the endothelial cells that make up the capillary walls are immediately adjacent to or very close to the material-host interface. There are no, or few, intervening macrophages or fibroblasts. Accordingly, molecules coming through the material will be at the surface of an endothelial cell for transportation into the capillaries. For example, molecules secreted by pancreatic islet cells on one side of the material will be available for uptake by capillaries on the other side of the material. Likewise, molecules such as glucose coming from the capillary, will be sensed by islet cells contained within an implanted chamber made of the material. The resistance to diffusion of such molecules will be related to the distance necessary to traverse the material.

Applicants tests of commercially available membranes (Tables 1–3) indicate that close vascular structures will likely result with a material having an average nominal pore size in the range of approximately 0.6 to about 20 microns and being composed of strands, fibers, cones, rods, or microglobules with a diameter no greater than approximately 5 microns.

Additional tests have shown that when the average aperture size is greater than approximately 40 microns, although vascular structures grow into the cavities of the membranes the capillaries are not in contact with or adjacent to the material but rather typically lie at some distance from the material due to a halo of macrophages and fibroblasts in a connective tissue matrix that surrounds the capillaries as illustrated in FIG. 3. Thus, as in the case of a foreign body capsule on the surface of a membrane, the capillaries are separated from the polymer surface by several layers of cells producing the same kind of diffusive resistance encountered in a classical foreign body response.

Figure 1A:
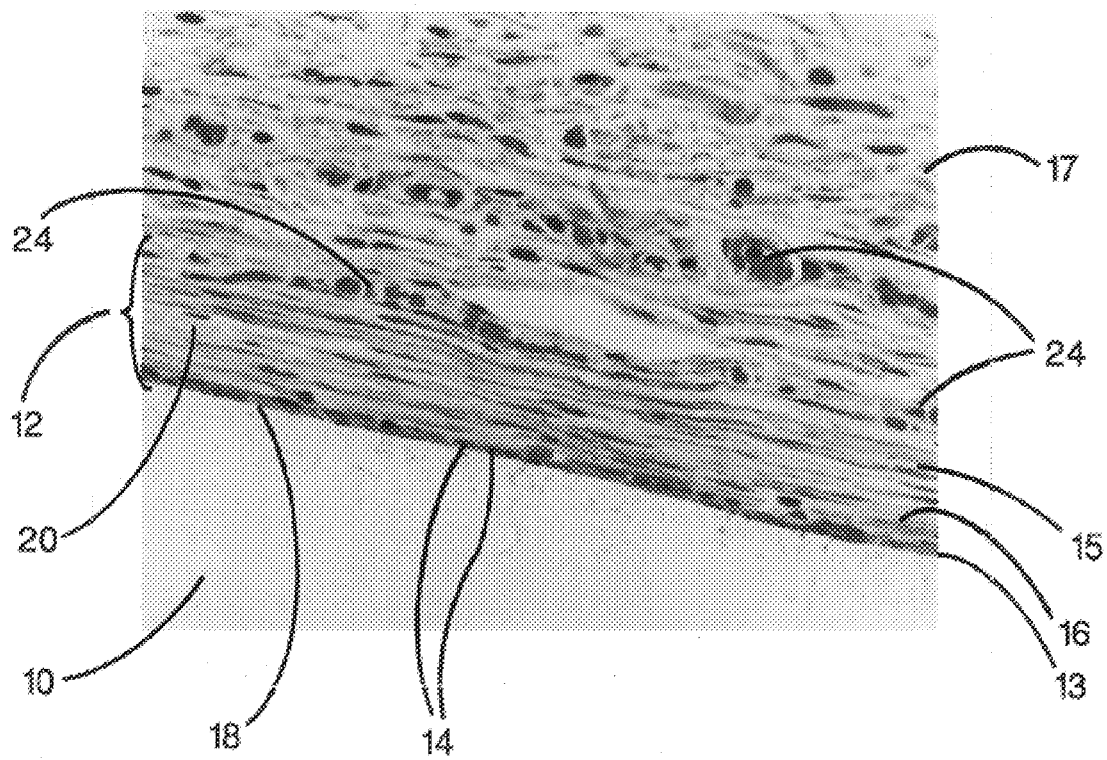
FIG. 1(a) is a micrograph that illustrates a classical foreign body response to an implanted device.
Figure 1B:
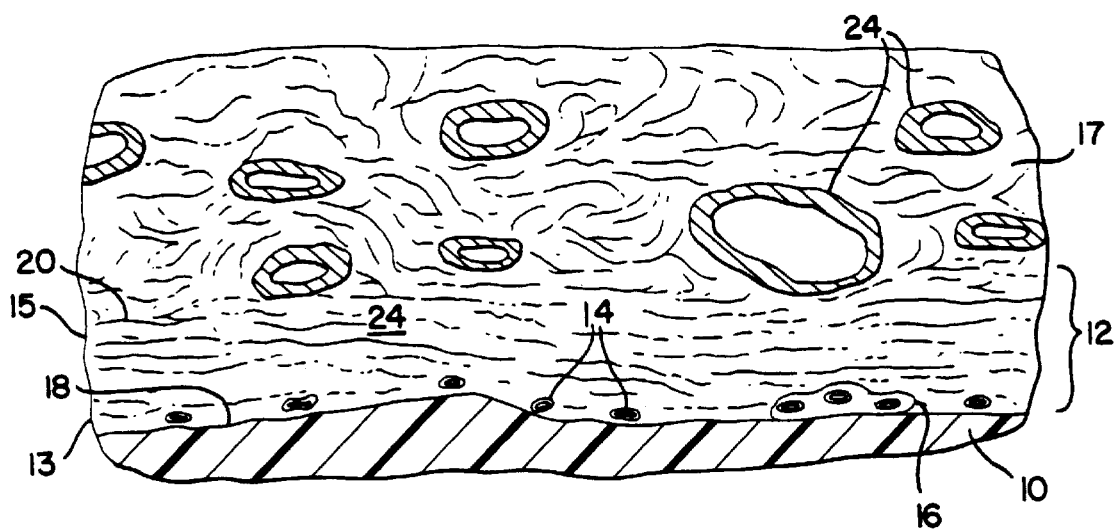
FIG. 1(b) is a drawing illustrating a classical foreign body response to an implanted device.

In contrast to the present invention, in a typical implant, the implant is encapsulated by the foreign body capsule and is typically at the edges of a large cellular avascular space, see FIG. 1.

The close vascularization of the present invention improves on previous biopolymer implants because the vascular bed is formed immediately adjacent to the material-host interface. As set forth in more detail below, this method of vascularization has a variety of applications. For example, the material can be used in conjunction with an indwelling sensor, an indwelling catheter, and for an immunoisolation container.

Figure 7:
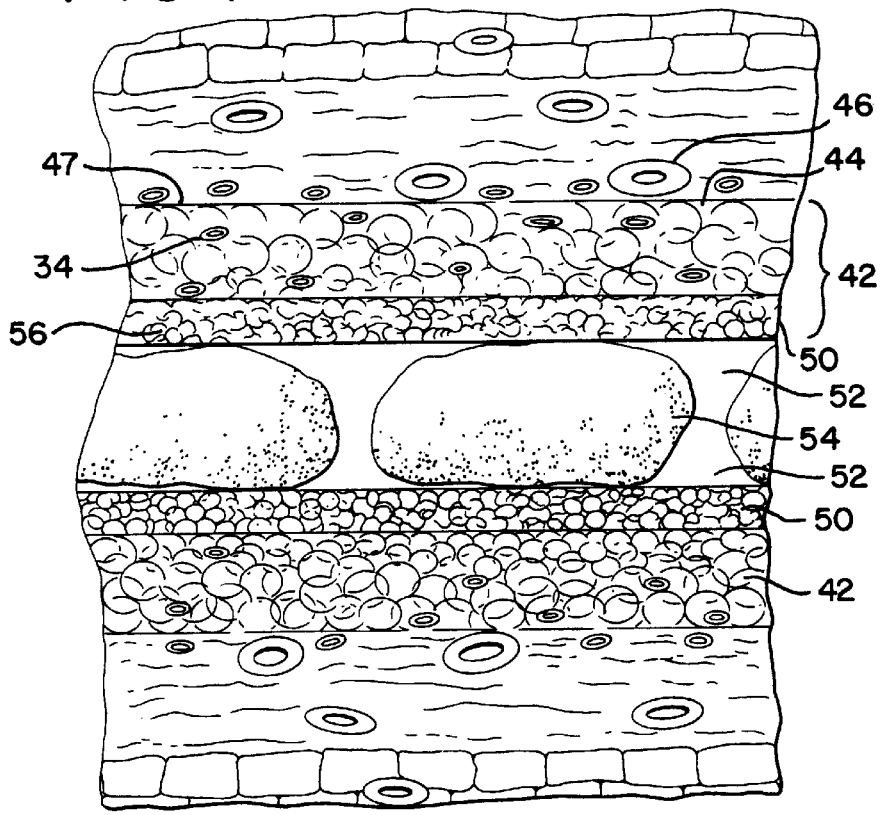
FIG. 7 illustrates a cross-sectional view of a bilaminar membrane containing islets, the membrane having an outer layer that is vascularized and an inner layer that prevents immune rejection.

Referring now to FIG. 7, an immunoisolation membrane 42 is illustrated. As illustrated, the membrane 42 is selected such that it allows macrophages 34 to enter at least some of the cavities 44 of the membrane causing vascular structures 46 to be formed at the host-membrane interface 47. Again, it should be noted that although some vascular structures can be formed within the cavities 44 of the membrane 42, this is not critical to the success of the material or the creation of a vascular bed.

As illustrated, the membrane 42 surrounds at least a portion of a second membrane or layer 50 that defines an immunoisolated interior 52. This interior 52 can include tissue 54 that must be protected from contact by host cells that would reject the implanted cells. For example, allografts or xenografts or in the case of isografts, such as autologous implants of genetically engineered cells, the membrane would need only to prevent passage of cells to prevent movement of the genetically engineered cells, which often contain retroviral vectors, out of the membrane enclosures and into the host tissues. This isolation of graft tissues from host tissue represents a significant advance over previous methods used for autologous transplantation of genetically engineered cells, because it prevents the genetically engineered cells from potentially invading host tissues in an unregulated manner and causing tumors in the host via the retroviral vector.

On the other hand, it is desirable that the second membrane 50 allow for the diffusion of components generated by the tissues 54, for example, insulin from pancreatic islets. Likewise, it is desirable that the second membrane 50 allow nutrients from the host to enter the interior 52 of the implant and nourish the tissue 54. To this end, the second membrane 50 preferably includes pores 56 that allow glucose or other components to diffuse into the first membrane 42 but prevents macrophages 34 and/or humoral factors from entering the second membrane.

Figure 8:
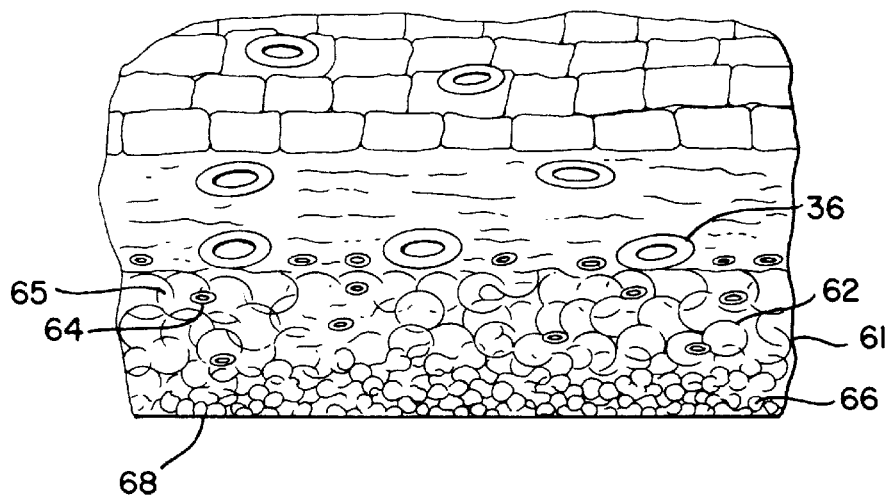
FIG. 8 illustrates a cross-sectional view of a further embodiment of the present invention.

Although the device illustrated in FIG. 7 includes two membrane layers, it should be noted that other constructions can be utilized. For example, referring to FIG. 8, the device includes a single membrane 61 that includes cavities 62 having a gradient of size. The larger outer cavities 62 allow macrophages to enter at least an outer portion 64 of the cavity 62, causing vascularization at the host-membrane interface 65. However, the smaller inner cavities 66 prevent macrophages from entering an inner portion of the membrane and thereby isolating an interior 68 defined by the membrane.

Figure 9:
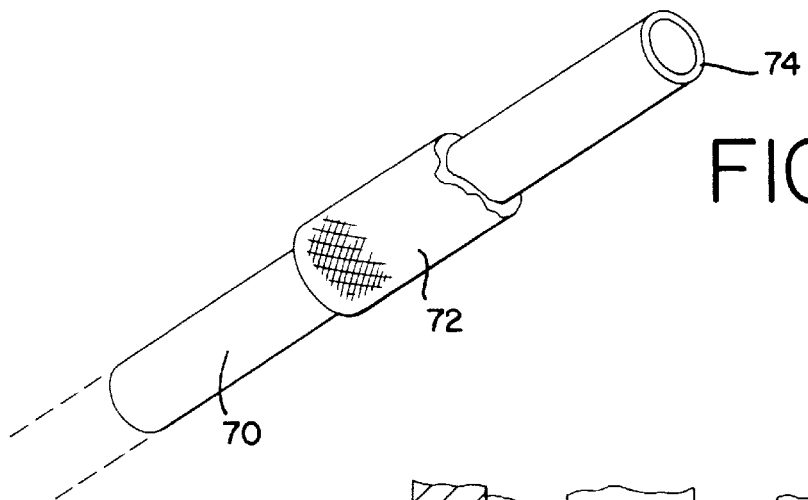
FIG. 9 illustrates an indwelling catheter incorporating the present invention.

Referring now to FIG. 9, an indwelling catheter 70 including an embodiment of the material 72 of the present invention is illustrated. Such a catheter 70 can be, for example, a catheter for continuous ambulatory peritoneal dialysis.

As illustrated, the material 72 covers the wall 74 of the catheter 70 and allows the creation of a vascular bed around the catheter 70. The wall 74 of the catheter 70 is preferably impenetrable to both cells and molecules.

In typical catheter designs, a thick foreign body of non-vascularized collagenous material is produced around the catheter that acts as a conduit for bacteria. In the present invention, vascularization around the catheter prevents tunnel site infections because necrosis of the tissue is prevented and the vascular bed bathes the area with the entire repertoire of blood borne immune cells. In another embodiment, a flange on a catheter would be covered with a vascularizing material, or would be made entirely from the material.

Figure 10:
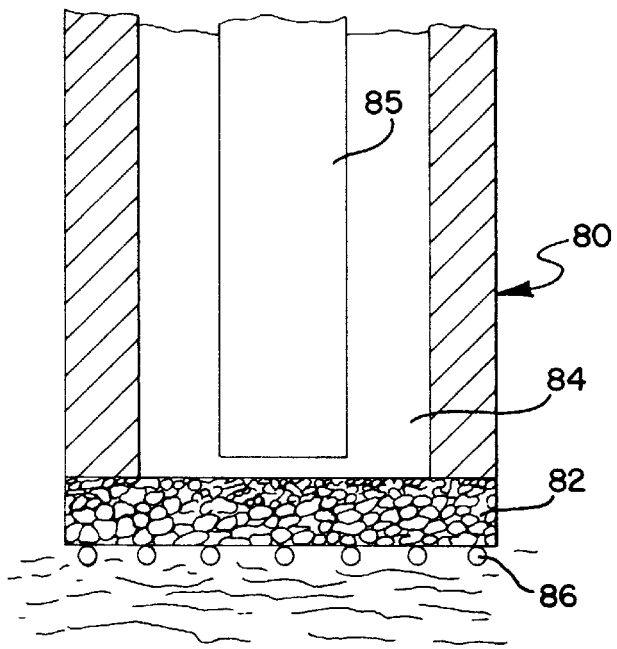
FIG. 10 illustrates an indwelling sensor incorporating the present invention.

Referring now to FIG. 10, a sensor 80 including an embodiment of the material 82 of the present invention is illustrated. Such a sensor 80 can include, for example, a glucose sensor for monitoring glucose levels in diabetics. As illustrated, the material 82 covers a body 84 which contains an electrode 85 of the sensor 80 and causes a vascular bed 86 to be created around the sensor 80. The creation of the vascular bed circumvents the problem of foreign body occlusion typically encountered with indwelling sensors.

The vascular response is believed to be unrelated to the composition of the material. This is illustrated by the above examples wherein similar responses of the tissue were found with respect to hydrophilic (cellulose) and hydrophobic (teflon) materials. Therefore, the inventors believe that the material can be constructed from a variety of polymers including, inter alia, polyethylene, polypropylene, teflon, cellulose acetate, cellulose nitrate, polycarbonate, polyester, nylon, polyester, polysulfone, mixed esters of cellulose polyvinylidene difluoride, silicone, and polyacrylonitrile. Known biocompatible medical implants are composed of ceramics and metals. Assuming these materials could be manipulated to provide the three dimensional structures described herein, they would also be useful in the present invention.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A device having a wall defining a chamber for holding living cells for implanting into a mammalian host wherein the wall comprises:

(a) a second zone of a material defining a chamber wherein the material is permeable to the flow of nutrients from the host to living cells and products from the living cells to the host and impermeable to host immune cells; and (b) a first zone of porous material outside of the second zone of material having a nominal pore size from about 0.6 to about 20 microns which comprises frames of elongated strands of material that are less than 5 microns in all but the longest dimension wherein said frames define apertures which interconnect to form three-dimensional cavities which permit substantially all inflammatory cells migrating into the cavities to maintain a rounded morphology, wherein the first zone promotes vascularization adjacent but not substantially into the first zone upon implantation into the host, and wherein the porous material is selected from the group consisting of polyethylene, polypropylene, polytetrafluoroethylene (PTFE), cellulose acetate, cellulose nitrate, polycarbonate, polyester, nylon, polysulfone, mixed esters of cellulose, polyvinylidene difluoride, silicone, and polyacrylonitrile.

2. A device having a wall defining a chamber for holding living cells for implanting into a mammalian host wherein the wall comprises:

(a) a second zone defining a chamber which is permeable to the flow of nutrients from the host to cells and products from the cells to the host and impermeable to host immune cells; and (b) a first zone outside of the second zone which comprises frames of elongated strands of material that are less than 5 microns in all but the longest dimension wherein said frames define apertures which interconnect to form three-dimensional cavities with interconnected apertures which permit substantially all inflammatory cells migrating into the cavities to maintain a rounded morphology, and wherein the first zone promotes vascularization adjacent but not substantially into the first zone upon implantation into the host.

3. The device according to claim 2, wherein the second zone comprises a porous material selected from the group consisting of polyethylene, polypropylene, polytetrafluoroethylene (PTFE), cellulose acetate, cellulose nitrate, polycarbonate, polyester, nylon, polysulfone, mixed esters of cellulose, polyvinylidene difluoride, silicone, and polyacrylonitrile.

4. The device according to claim 3, wherein the second zone comprises porous material having a nominal porous size about 0.6 to about 20 microns.

5. The device according to claims 1 or 2, wherein said second zone is further impermeable to immune factors.

* * * * *